(12) United States Patent  
Alrajhi

(10) Patent No.: US 11,931,597 B1
(45) Date of Patent: Mar. 19, 2024

(54) INTRAORAL RADIOTHERAPY STENT

(71) Applicant: KING SAUD UNIVERSITY, Riyadh (SA)

(72) Inventor: Farah Nasser Alrajhi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/224,291

(22) Filed: Jul. 20, 2023

(51) Int. Cl.
*A61C 5/90* (2017.01)
*A61N 5/10* (2006.01)

(52) U.S. Cl.
CPC .............. *A61N 5/1014* (2013.01); *A61C 5/90* (2017.02)

(58) Field of Classification Search
CPC .. A61C 5/90; A61C 17/10; A61B 1/24; A61N 2005/1094
See application file for complete search history.

(56) References Cited

U.S. PATENT DOCUMENTS

| 1,415,347 | A | * | 5/1922 | Heidbrink | A61B 1/24 |
| | | | | | 600/238 |
| 2,937,445 | A | * | 5/1960 | Erickson | A61B 1/24 |
| | | | | | 433/93 |
| 3,916,880 | A | * | 11/1975 | Schroer | A61C 17/10 |
| | | | | | 600/242 |
| 4,887,965 | A | * | 12/1989 | Fox | A61B 1/24 |
| | | | | | 433/140 |
| 5,037,298 | A | * | 8/1991 | Hickham | A61C 5/90 |
| | | | | | 433/93 |
| 9,504,537 | B2 | | 11/2016 | Johnson et al. | |
| 9,901,332 | B2 | * | 2/2018 | Jessop | A61B 1/32 |
| 10,363,004 | B2 | | 7/2019 | Holman et al. | |
| 10,729,524 | B2 | | 8/2020 | Brawn et al. | |
| 2004/0209225 | A1 | * | 10/2004 | Kilcher | A61C 5/90 |
| | | | | | 433/140 |
| 2005/0227199 | A1 | * | 10/2005 | Patrickus | A61C 17/10 |
| | | | | | 433/93 |
| 2006/0069316 | A1 | * | 3/2006 | Dorfman | A61C 5/90 |
| | | | | | 600/237 |
| 2007/0156028 | A1 | | 7/2007 | Van Lue et al. | |
| 2012/0012120 | A1 | | 1/2012 | Giffey et al. | |
| 2012/0183920 | A1 | * | 7/2012 | Shluper | A61C 19/066 |
| | | | | | 433/31 |

(Continued)

FOREIGN PATENT DOCUMENTS

DE 836231 * 4/1952

*Primary Examiner* — Ralph A Lewis
(74) *Attorney, Agent, or Firm* — Nath, Goldberg & Meyer; Richard C. Litman

(57) ABSTRACT

The intraoral radiotherapy stent includes a hollow tube having opposed first and second open ends. First and second discs are provided, each having opposed inner and outer faces. A first shaft is secured centrally to the inner face of the first disc and extends axially therefrom. The first shaft is adjustably received within the hollow tube through the first open end thereof. A second shaft is secured centrally to the inner face of the second disc and extends axially therefrom. The second shaft is adjustably received within the hollow tube through the second open end thereof. First and second lip retractors are mounted on the hollow tube for holding the patient's mount open during a radiotherapy procedure or the like, and a tongue depressor is also mounted on the hollow tube to depress the patient's tongue and minimize tongue movement during radiotherapy or the like.

17 Claims, 2 Drawing Sheets

(56) References Cited

U.S. PATENT DOCUMENTS

| | | | |
|---|---|---|---|
| 2013/0006097 A1* | 1/2013 | Mick | A61N 5/1016 |
| | | | 600/414 |
| 2018/0028292 A1* | 2/2018 | Pesach | A61C 9/004 |
| 2019/0262110 A1 | 8/2019 | Wakefield | |
| 2020/0375696 A1* | 12/2020 | Jessop | A61B 1/24 |
| 2022/0266060 A1 | 8/2022 | Maresca et al. | |

* cited by examiner

INTRAORAL RADIOTHERAPY STENT

BACKGROUND OF THE INVENTION

Field of the Invention

The disclosure of the present patent application relates to radiotherapy, and particularly to an intraoral stent for use during radiotherapy to protect healthy structures adjacent the target area of head and neck radiotherapy treatment.

Description of Related Art

Oral positioning radiotherapy stents are devices that protect healthy structures adjacent to an area targeted by head and neck radiotherapy treatment, leading to reduced acute and chronic side effects. During radiation therapy treatment to the head and neck, patients often suffer from acute sequelae in the form of xerostomia, mucositis, loss of taste, and radiation-induced dermatitis. Mucositis usually starts during the second week of radiation therapy and progresses as the treatment continues. Mucositis can cause pain, odynophagia, dysphagia, periodontal disease, fungal infection, poor oral intake which necessitates alternative methods of feeding, and can result in treatment interruption.

In recent years, advances in radiation therapy delivery and techniques have been made to reduce the occurrence of acute sequelae while maintaining adequate treatment dose delivery to the target area. Intensity modulated radiation therapy (IMRT) and image guided radiation therapy (IGRT) are currently used for greater accuracy to minimize damage to the adjacent untreated tissues. However, despite these new treatment methods, patients often still develop acute mucositis due to the proximity of the normal mucosal surface to the target area. Increasing the distance between the normal mucosal tissue and the treatment area can significantly reduce the radiation dose and, correspondingly, the degree of mucositis.

In order to provide spacing and shielding for the normal mucosal tissue, a wide variety of oral stents have been used. Such stents are typically relatively simple devices, either including or used in combination with lip retractors for holding the patient's mouth open. Typical stents focus on depressing and stabilizing the patient's tongue, with the buccal mucosa being held out of the way primarily by the lip retractors. Unfortunately, the usage of the lip retractors alone does not fully prevent the buccal mucosa from being irradiated, thus still often resulting in the patient developing mucositis. Thus, an intraoral radiotherapy stent solving the aforementioned problems is desired.

SUMMARY OF THE INVENTION

The intraoral radiotherapy stent includes a hollow tube having opposed first and second open ends and which is adapted for reception within a patient's mouth such that it is oriented to extend from one buccal mucosa to the other. First and second discs are provided, each having opposed inner and outer faces. A first shaft is secured centrally to the inner face of the first disc and extends axially therefrom. The first shaft is adjustably received within the hollow tube through the first open end thereof. A second shaft is secured centrally to the inner face of the second disc and extends axially therefrom. The second shaft is adjustably received within the hollow tube through the second open end thereof. The first and second discs are adapted for contacting and displacing the patient's buccal mucosa outward in an adjustable manner. As a non-limiting example, a threaded bore may be formed through the hollow tube, with each of the first and second shafts being threaded for adjustably engaging the threaded bore. Thus, the spacing between the two discs and, correspondingly, the degree to which the patient's buccal mucosa are pushed outward, can be adjusted by rotating the discs.

First and second lip retractors are mounted on the hollow tube for holding the patient's mouth open during a radiotherapy procedure or the like. First and second mounts may be secured to the hollow tube, adjacent the first and second open ends of the hollow tube, respectively, with the first lip retractor being secured to the first mount and the second lip retractor being secured to the second mount. Each of the first and second mounts may project forwardly from the hollow tube such that the first and second lip retractors are positioned forward of the hollow tube, allowing the hollow tube and the first and second discs to be positioned within the patient's mouth, behind the first and second lip retractors.

A tongue depressor may also be mounted on the hollow tube to depress the patient's tongue and minimize tongue movement during radiotherapy or the like. The tongue depressor may project forwardly from the hollow tube and be positioned between the first and second mounts.

Additionally, first and second bite blocks may be mounted on the hollow tube. The first and second bite blocks may be positioned adjacent to the first and second open ends of the hollow tube, respectively, and may project upwardly from the hollow tube. The first and second bite blocks are each adapted for the teeth to occlude thereupon in dentate patients, thus opening the maxillary and mandibular bites.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

Figure 1:
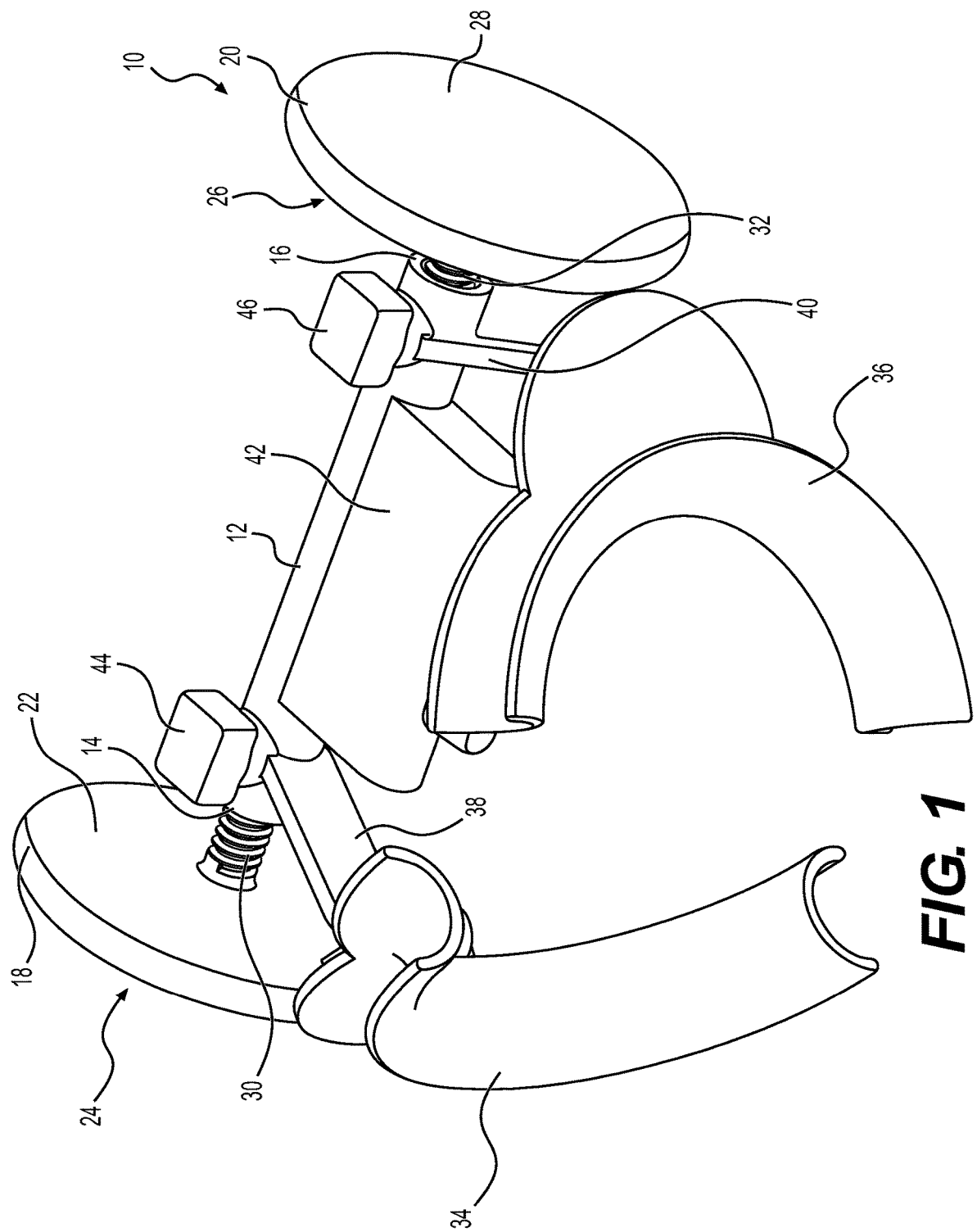
FIG. 1 is a front perspective view of the intraoral radiotherapy stent.
Figure 2:
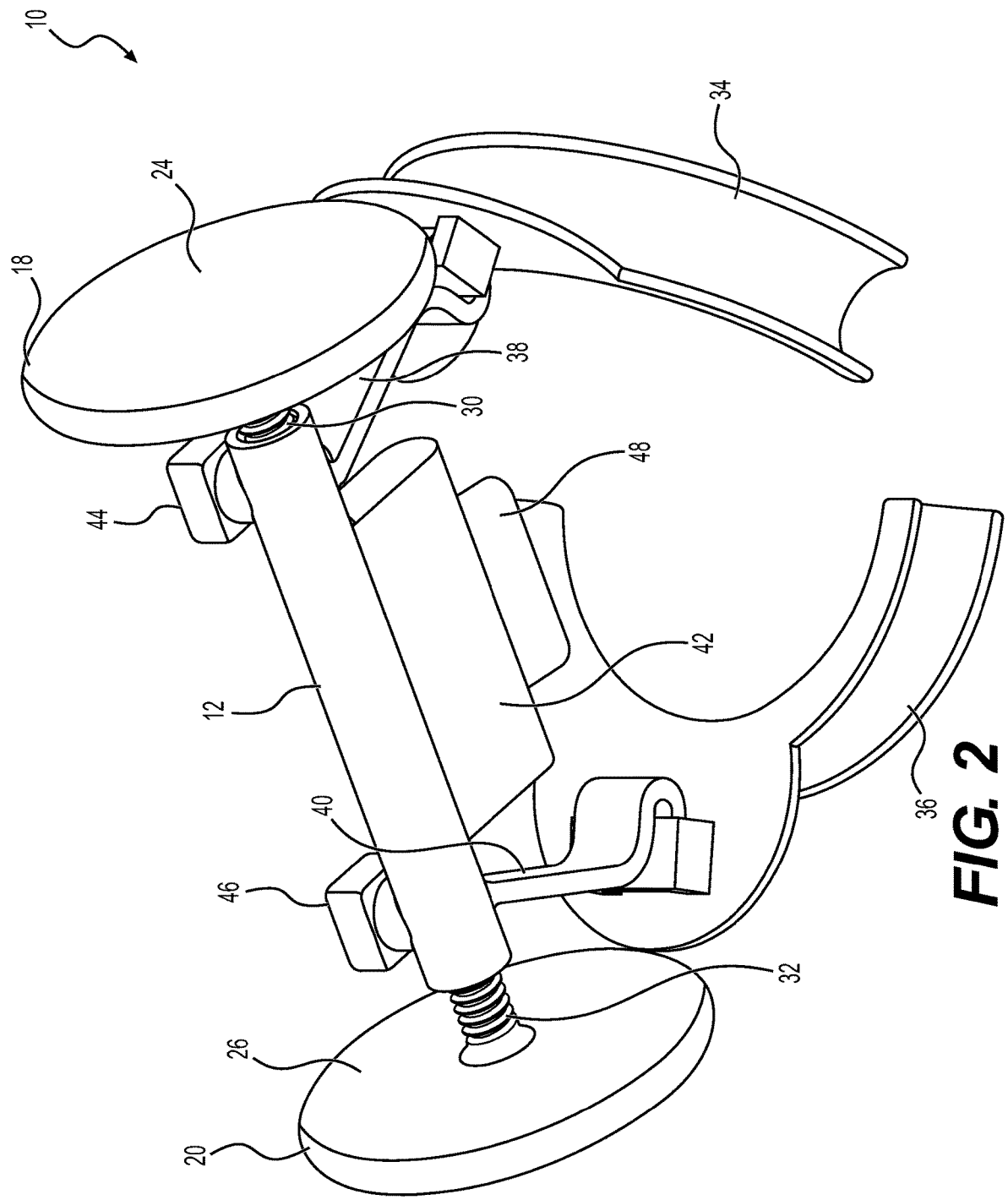
FIG. 2 is a rear perspective view of the intraoral radiotherapy stent.

As shown in FIGS. 1 and 2, the intraoral radiotherapy stent 10 includes a hollow tube 12 having opposed first and second open ends 14, 16, respectively, and which is adapted for reception within a patient's mouth such that it is oriented to extend from one buccal mucosa to the other. It should be understood that the relative dimensions of hollow tube 12 are shown in FIGS. 1 and 2 for exemplary purposes only and may be varied. A first disc 18 has opposed inner and outer faces 22, 24, respectively, and a second disc 20 has opposed inner and outer faces 26, 28, respectively. It should be understood that the relative dimensions of first and second discs 18, 20 are shown in FIGS. 1 and 2 for exemplary purposes only and may be varied. A first shaft 30 is secured centrally to the inner face 22 of the first disc 18 and extends axially therefrom. The first shaft 30 is adjustably received within the hollow tube 12 through the first open end 14. A second shaft 32 is secured centrally to the inner face 26 of the second disc 20 and extends axially therefrom. The second shaft 32 is adjustably received within the hollow tube 12 through the second open end 16. The first and second discs 18, 20 are adapted for contacting and displacing the patient's buccal mucosa outwardly in an adjustable manner. As a non-limiting example, a threaded bore may be formed through the hollow tube 12, with each of the first and second shafts 30, 32, respectively, being threaded for adjustably engaging the threaded bore, as illustrated in FIGS. 1 and 2. Thus, the spacing between the first and second discs 18, 20 and, correspondingly, the degree to which the patient's buccal mucosa are pushed outwardly, can be adjusted by rotating one or both of the first and second discs 18, 20.

First and second lip retractors 34, 36, respectively, are mounted on the hollow tube 12 for holding the patient's mouth open during a radiotherapy procedure or the like. First and second mounts 38, 40 may be secured to the hollow tube 12, adjacent the first and second open ends 14, 16 of the hollow tube 12, respectively, with the first lip retractor 34 being secured to the first mount 38 and the second lip retractor 36 being secured to the second mount 40. Each of the first and second mounts 38, 40, respectively, may project forwardly from the hollow tube 12 such that the first and second lip retractors 34, 36 are positioned forward of the hollow tube 12 (i.e., in the anterior direction), allowing the hollow tube 12 and the first and second discs 18, 20 to be positioned within the patient's mouth, behind the first and second lip retractors 34, 36 (i.e., inferior to the patient's mouth). It should be understood that the shape, relative dimensions and overall configuration of both the first and second lip retractors 34, 36 and the first and second mounts 38, 40 are shown in FIGS. 1 and 2 for exemplary purposes only and may be varied.

A tongue depressor 42 may also be mounted on the hollow tube 12 to depress the patient's tongue and minimize tongue movement during radiotherapy or the like. The tongue depressor 42 may project forwardly from the hollow tube 12 and be positioned between the first and second mounts 38, 40. As best seen in FIG. 2, a smaller anteriorly projecting member 48 may be mounted on the tongue depressor 42 for better stabilizing the forward portion of the patient's tongue, adjacent the tip thereof. It should be understood that the shape and relative dimensions of tongue depressor 42 and projecting member 48 are shown for exemplary purposes only and may be varied.

Additionally, first and second bite blocks 44, 46, respectively, may be mounted on the hollow tube 12. The first and second bite blocks 44, 46 may be positioned adjacent the first and second open ends 14, 16 of the hollow tube 12, respectively, and may project upwardly from the hollow tube 12, as shown. The first and second bite blocks 44, 46 are each adapted for the teeth to occlude thereupon in dentate patients, thus opening the maxillary and mandibular bites. It should be understood that the shape and relative dimensions of the first and second bite blocks 44, 46 are shown in FIGS. 1 and 2 for exemplary purposes only and may be varied.

It is to be understood that the intraoral radiotherapy stent is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. An intraoral radiotherapy stent, comprising:
a hollow tube having opposed first and second open ends, said hollow tube being adapted to be received within a patient's mouth and oriented such that said hollow tube is adapted to extend from a first buccal mucosa to a second buccal mucosa within the patient's mouth;
first and second discs each having opposed inner and outer faces wherein the outer face of said first disc and the outer face of said second disc are adapted for contacting and outwardly displacing said first buccal mucosa and said second buccal mucosa in an adjustable manner, respectively;
a first shaft secured centrally to the inner face of the first disc and extending axially therefrom, the first shaft being adjustably received within the hollow tube through the first open end thereof;
a second shaft secured centrally to the inner face of the second disc and extending axially therefrom, the second shaft being adjustably received within the hollow tube through the second open end thereof; and
first and second lip retractors mounted on the hollow tube.

2. The intraoral radiotherapy stent as recited in claim 1, wherein a threaded bore is formed through the hollow tube, and wherein each of the first and second shafts is threaded for adjustably engaging the threaded bore.

3. The intraoral radiotherapy stent as recited in claim 1, further comprising first and second mounts secured to the hollow tube adjacent the first and second open ends of the hollow tube, respectively, the first lip retractor being secured to the first mount and the second lip retractor being secured to the second mount.

4. The intraoral radiotherapy stent as recited in claim 3, wherein each of the first and second mounts projects forwardly from the hollow tube.

5. The intraoral radiotherapy stent as recited in claim 4, further comprising a tongue depressor mounted on the hollow tube.

6. The intraoral radiotherapy stent as recited in claim 5, wherein the tongue depressor projects forwardly from the hollow tube and is positioned between the first and second mounts.

7. The intraoral radiotherapy stent as recited in claim 1, further comprising first and second bite blocks mounted on the hollow tube.

8. The intraoral radiotherapy stent as recited in claim 7, wherein the first and second bite blocks are positioned adjacent the first and second open ends of the hollow tube, respectively.

9. The intraoral radiotherapy stent as recited in claim 8, wherein each of the first and second bite blocks projects upwardly from the hollow tube.

10. An intraoral radiotherapy stent, comprising:
a hollow tube having opposed first and second open ends, said hollow tube being adapted to be received within a patient's mouth and oriented such that said hollow tube is adapted to extend from a first buccal mucosa to a second buccal mucosa within the patient's mouth;
first and second discs each having opposed inner and outer faces, wherein the outer face of said first disc and the outer face said second disc are adapted for contacting and outwardly displacing said first buccal mucosa and said second buccal mucosa in an adjustable manner, respectively;
a first shaft secured centrally to the inner face of the first disc and extending axially therefrom, the first shaft being adjustably received within the hollow tube through the first open end thereof;
a second shaft secured centrally to the inner face of the second disc and extending axially therefrom, the second shaft being adjustably received within the hollow tube through the second open end thereof;
first and second lip retractors mounted on the hollow tube; and
a tongue depressor mounted on the hollow tube.

11. The intraoral radiotherapy stent as recited in claim 10, wherein a threaded bore is formed through the hollow tube, and wherein each of the first and second shafts is threaded for adjustably engaging the threaded bore.

12. The intraoral radiotherapy stent as recited in claim 10, further comprising first and second mounts secured to the hollow tube adjacent the first and second open ends of the hollow tube, respectively, the first lip retractor being secured to the first mount and the second lip retractor being secured to the second mount.

13. The intraoral radiotherapy stent as recited in claim 12, wherein each of the first and second mounts projects forwardly from the hollow tube.

14. The intraoral radiotherapy stent as recited in claim 13, wherein the tongue depressor projects forwardly from the hollow tube and is positioned between the first and second mounts.

15. The intraoral radiotherapy stent as recited in claim 10, further comprising first and second bite blocks mounted on the hollow tube.

16. The intraoral radiotherapy stent as recited in claim 15, wherein the first and second bite blocks are positioned adjacent the first and second open ends of the hollow tube, respectively.

17. The intraoral radiotherapy stent as recited in claim 16, wherein each of the first and second bite blocks projects upwardly from the hollow tube.

\* \* \* \* \*